(12) United States Patent
Bouasaysy et al.

(10) Patent No.: US 12,426,903 B2
(45) Date of Patent: Sep. 30, 2025

(54) RE-ENTRY CATHETER

(71) Applicant: ReFlow Medical, Inc., San Clemente, CA (US)

(72) Inventors: Outhit Bouasaysy, Corona, CA (US); John Fulkerson, Rancho Santa Margarita, CA (US); Isa Rizk, San Diego, CA (US); Fadi Saab, Ada, MI (US)

(73) Assignee: ReFlow Medical, Inc., San Clemente, CA (US)

( * ) Notice: Subject to any disclaimer, the term of this patent is extended or adjusted under 35 U.S.C. 154(b) by 320 days.

(21) Appl. No.: 17/991,669

(22) Filed: Nov. 21, 2022

(65) Prior Publication Data

US 2023/0091211 A1 Mar. 23, 2023

Related U.S. Application Data

(63) Continuation-in-part of application No. 16/993,145, filed on Aug. 13, 2020, now Pat. No. 11,504,142.

(60) Provisional application No. 62/886,239, filed on Aug. 13, 2019.

(51) Int. Cl.
*A61B 17/22* (2006.01)
*A61B 17/00* (2006.01)
*A61M 25/00* (2006.01)

(52) U.S. Cl.
CPC ......... *A61B 17/22* (2013.01); *A61M 25/0043* (2013.01); *A61B 2017/00336* (2013.01); *A61B 2017/22042* (2013.01); *A61M 2025/0004* (2013.01)

(58) Field of Classification Search
CPC ......... A61B 17/22; A61B 2017/22038; A61M 25/007; A61M 25/0108; A61M 25/0194; A61M 25/09; A61M 2025/0018; A61M 2025/0183; A61M 2025/0197
USPC .......................................................... 606/159
See application file for complete search history.

(56) References Cited

U.S. PATENT DOCUMENTS

| 4,552,554 | A | * | 11/1985 | Gould | A61M 25/01 604/164.13 |
|---|---|---|---|---|---|
| 6,022,342 | A | | 2/2000 | Mukherjee | |
| 6,585,650 | B1 | * | 7/2003 | Solem | A61F 2/064 606/7 |

(Continued)

FOREIGN PATENT DOCUMENTS

| JP | 2003-527192 | 9/2003 |
|---|---|---|
| JP | 2008-509726 | 4/2008 |

(Continued)

OTHER PUBLICATIONS

International Search Report and Written Opinion from PCT/US2020/046232, dated Dec. 3, 2020, 17 pages.

(Continued)

*Primary Examiner* — Jocelin C Tanner
(74) *Attorney, Agent, or Firm* — BAKERHOSTETLER

(57) ABSTRACT

A delivery system can be provided with an ability to change its configurations to achieve both access to target anatomy and treatment thereof. Such treatments can include directing interventional devices around an occlusion. By providing different functionality at different stages, the need to exchange and replace tools at different stages can be reduced or eliminated. Accordingly, such operations can be completed more rapidly, efficiently, and safely.

20 Claims, 10 Drawing Sheets

(56) References Cited

U.S. PATENT DOCUMENTS

| | | |
|---|---|---|
| 7,179,270 B2 | 2/2007 | Makower |
| 10,098,650 B2 | 10/2018 | Kangas et al. |
| 2001/0000041 A1 | 3/2001 | Selmon et al. |
| 2003/0045836 A1 | 3/2003 | Batiste |
| 2003/0153934 A1* | 8/2003 | Gerberding ....... A61M 25/0169 606/157 |
| 2006/0036233 A1 | 2/2006 | Boutillette |
| 2006/0047335 A1 | 3/2006 | Israel |
| 2006/0276749 A1 | 12/2006 | Selmon et al. |
| 2009/0182200 A1 | 7/2009 | Golden |
| 2012/0095485 A1 | 4/2012 | Cully et al. |
| 2018/0056046 A1 | 3/2018 | Kiersey |
| 2018/0333162 A1 | 11/2018 | Saab |
| 2019/0134349 A1 | 5/2019 | Cohn |
| 2020/0129143 A1 | 4/2020 | Di Tullio et al. |

FOREIGN PATENT DOCUMENTS

| | | |
|---|---|---|
| JP | 2003-544561 | 12/2013 |
| JP | 2018-130313 | 8/2018 |
| WO | WO 93/005841 A1 | 4/1993 |
| WO | WO 01/70133 | 9/2001 |
| WO | WO 2019/046537 A2 | 3/2019 |

OTHER PUBLICATIONS

Australian Examination Report from Australian Patent Application No. 2020328042, dated Jan. 17, 2025, 4 pages.

Chinese Office Action from Chinese Patent Application No. 202080071973.8, dated Mar. 15, 2024, 17 pages including English language translation.

Japanese Office Action from Japanese Patent Application No. 2022-508981, dated May 1, 2024, 8 pages including English language translation.

Chinese Office Action from 202080071973.8, dated Aug. 21, 2024, 18 pages including machine-generated English language translation.

European Patent Application No. 20761978.4, Office Action dated May 30, 2025, 5 pages.

* cited by examiner

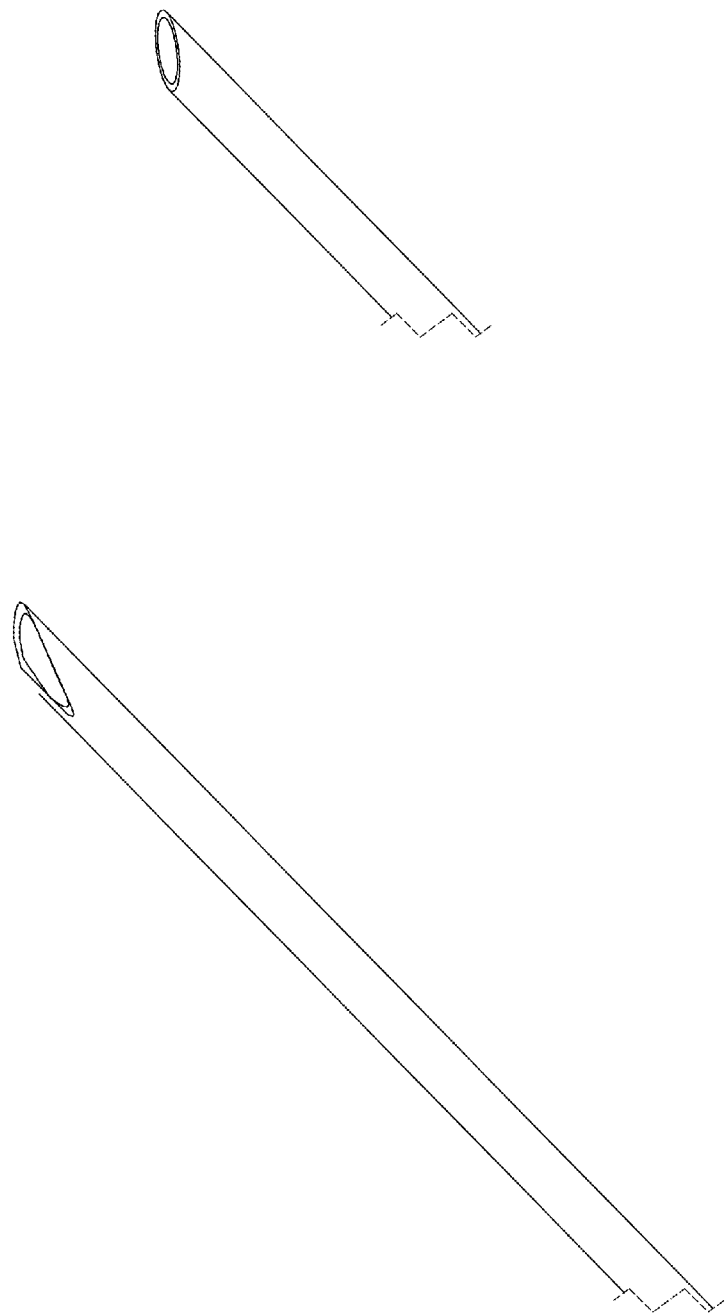

RE-ENTRY CATHETER

CROSS-REFERENCE TO RELATED APPLICATION

This application is a continuation-in-part of U.S. application Ser. No. 16/993,145, entitled "RE-ENTRY CATHETER," filed Aug. 13, 2020, which claims the benefit of U.S. Provisional Application No. 62/886,239, entitled "RE-ENTRY CATHETER," filed Aug. 13, 2019, the entirety of each of which is hereby incorporated herein by reference.

TECHNICAL FIELD

The present description relates in general to treatment of stenosis in a body vessel and in particular to catheters and methods for crossing a chronic total occlusion in a blood vessel.

BACKGROUND OF THE DISCLOSURE

Chronic total occlusions ("CTO") are vascular lesions characterized by heavy atherosclerotic plaque within the blood vessel, resulting in complete (or nearly complete) obstruction of blood flow across the lesion. Such occlusions can occur anywhere in a patient's vascular system. Since most lesions form gradually over a long period of time, the ischemic tissue downstream of the lesion has time to form collateral circulation. For example, in the case of coronary arteries, collateral vessels can form from the proximal artery and connect into the distal artery ("ipsilateral collaterals"), or collateral vessels can form from the other major arterial branches and connect into the distal artery ("contralateral collaterals"). When the lesion finally becomes a total occlusion, the collateral circulation is typically sufficient to keep the distal tissue alive, though ischemic. Accordingly, it is desirable to reestablish blood flow through or around the blockage in blood vessels by crossing the CTO and advancing therapeutic devices, such as a balloon angioplasty catheter, to dilate and treat the CTO. Likewise, in some cases it may be necessary to cross a CTO to gain access to a location along the vasculature distal to the CTO. CTOs can be more difficult to cross than partially occluded lesions because, rather than navigate a pre-existing lumen, a guidewire must either penetrate the lesion or, when penetrating the occlusion is impractically difficult and/or complicated, go around the lesion via a sub-intimal layer of a vessel wall.

The description provided in the background section should not be assumed to be prior art merely because it is mentioned in or associated with the background section. The background section may include information that describes one or more aspects of the subject technology.

BRIEF DESCRIPTION OF THE DRAWINGS

FIG. 19 is a schematic view of an embodiment of a blade of a crossing device, according to embodiments of the present disclosure.

FIG. 20 is a schematic view of an embodiment of a blade of a crossing device, according to embodiments of the present disclosure.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various implementations and is not intended to represent the only implementations in which the subject technology may be practiced. As those skilled in the art would realize, the described implementations may be modified in various different ways, all without departing from the scope of the present disclosure. Accordingly, the drawings and description are to be regarded as illustrative in nature and not restrictive.

The present technology relates generally to systems, methods, and devices for crossing and treating CTOs. While CTOs are discussed, it will be understood that the devices and methods described herein can facilitate treatment of a variety of conditions.

It can be desirable to provide a system and/or devices that facilitate access to target anatomy (e.g., CTO in a blood vessel) and further facilitate an intervention for restoring flow across the CTO. Various stages of such operations may involve the operation of multiple tools to access, cross, and treat the target anatomy. The systems and methods described herein are directed to devices that provide multiple functions at different stages. By providing different functionality at different stages, the need to exchange and replace tools at different stages can be reduced or eliminated. Accordingly, such operations can be completed more rapidly, efficiently, and safely.

Specific details of several embodiments of the present technology are described herein with reference to FIGS. 1-11. Although many of the embodiments are described below with respect to devices and methods for crossing and/or treating CTOs, any vascular occlusion in addition to those described herein may be crossed and/or treated within the scope of the present technology (e.g., full occlusions, partial occlusions, occlusions resulting from a thrombus, occlusions resulting from an embolism, occlusions resulting from atherosclerosis, etc.). Additionally, other embodiments of the present technology can have different configurations, components, or procedures than those described herein. For example, other embodiments can include additional elements and features beyond those described herein, or other embodiments may not include several of the elements and features shown and described herein.

Figure 1:
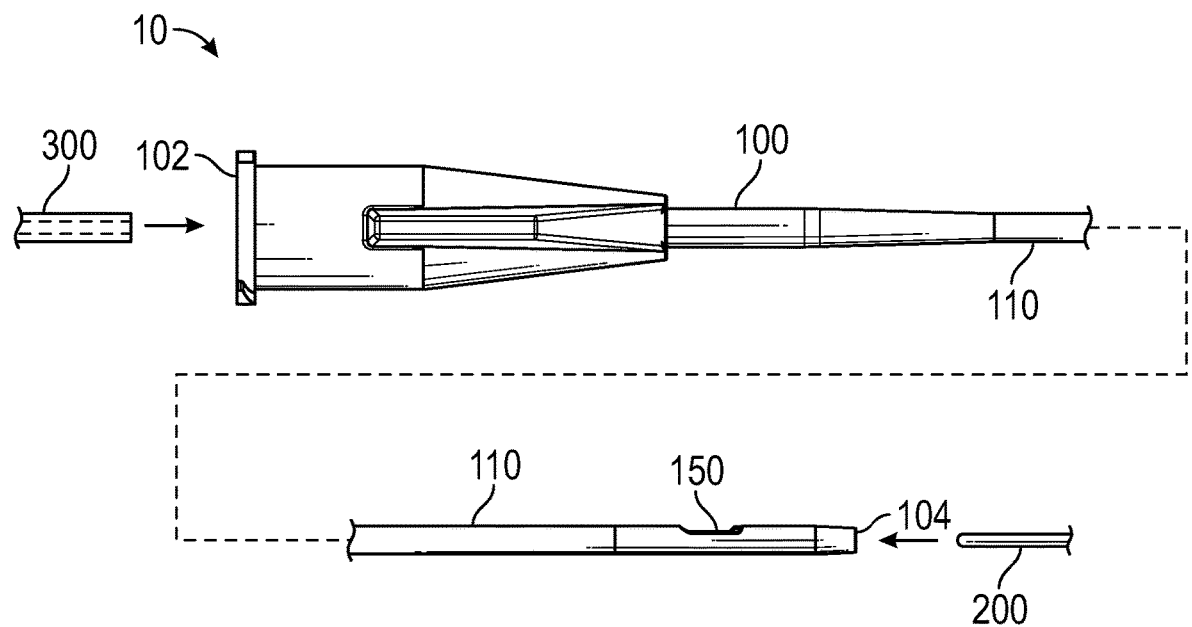
FIG. 1 illustrates a side view of a delivery device.

As shown in FIG. 1, a system can include a delivery device 100 for delivering another device through a lumen thereof. The delivery device 100 can include a connector 106 at and/or defining a proximal end portion 102 of the delivery device 100 and providing a handle, luer, connector, and/or hub. For example, the connector 106 can include a mating feature and/or a receiving feature for securely coupling to other components. The connector 106 can include a touhy bourst seal configured to secure a position of one or more devices within the delivery device 100.

The delivery device 100 can further include a distal tip 190 at and/or defining a distal end portion 104 of the delivery device 100. The distal tip 190 can include a radiopaque distal tip (e.g., polymer, tungsten, barium, etc.). The delivery device 100 can further include a shaft 110 extending between the connector 106 and the distal tip 190. The connector 106 can be configured to be positioned at a location external to a patient, and the shaft 110 can be configured to position the distal tip 190 (e.g., intravascularly) at or near a complete or partial occlusion within a blood vessel of the patient. The delivery device 100 can have a lumen extending from the connector 106 to the distal tip 190 and/or a side port 150. The delivery device 100 can include a strain relief element between the shaft 110 and another portion at the connector 106. For example, the strain relief element can surround or otherwise engage the shaft 110 at a proximal end thereof.

The delivery device 100 can receive one or more devices (e.g., guidewire 200) into the lumen through the distal end portion 104. The delivery device 100 can receive one or more devices (e.g., crossing device 300) into the lumen through the proximal end portion 102.

The shaft 110 can be sized and shaped for intravascularly accessing a target site (e.g., treatment site) of the patient. In some embodiments, for example, the shaft 110 has a length of about 150 cm to about 180 cm and a suitable cross-sectional dimension for positioning within a subject's vasculature. The length of the shaft 110 can be a working length, such as a length that can be positioned within a subject's vasculature. In some embodiments, for example, the working length is about 70 cm to about 300 cm, about 150 cm to about 250 cm, or about 70 cm, about 80 cm, about 90 cm, about 100 cm, about 110 cm, about 120 cm, about 130 cm, about 140 cm, about 150 cm, about 160 cm, about 170 cm, about 180 cm, about 190 cm, about 200 cm, about 210 cm, about 220 cm, about 230 cm, about 240 cm, about 250 cm, about 260 cm, about 270 cm, about 280 cm, about 290 cm, or about 300 cm.

Figure 2:
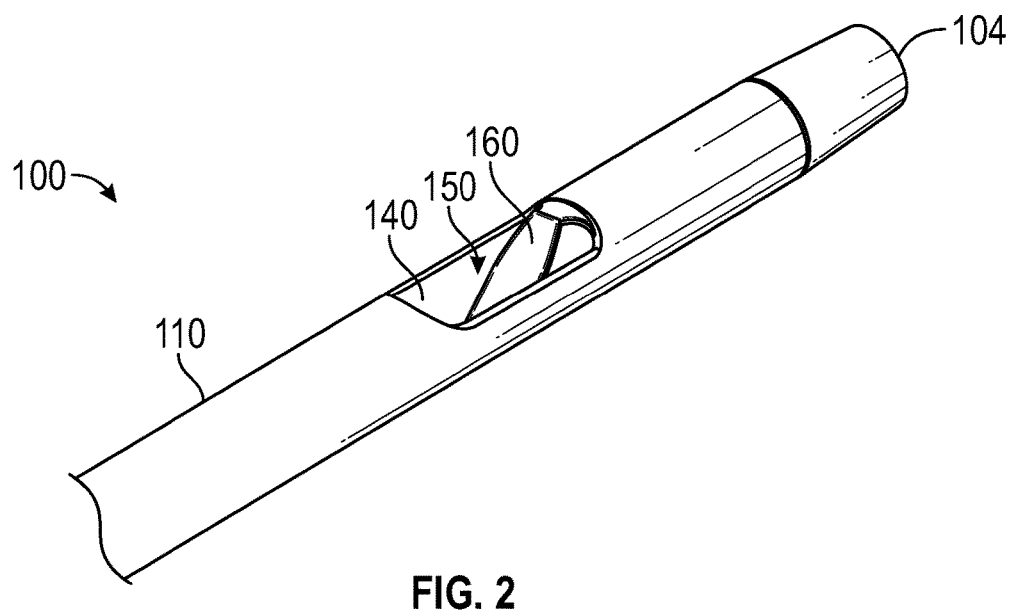
FIG. 2 illustrates a perspective view of a distal portion of a delivery device.
Figure 3:
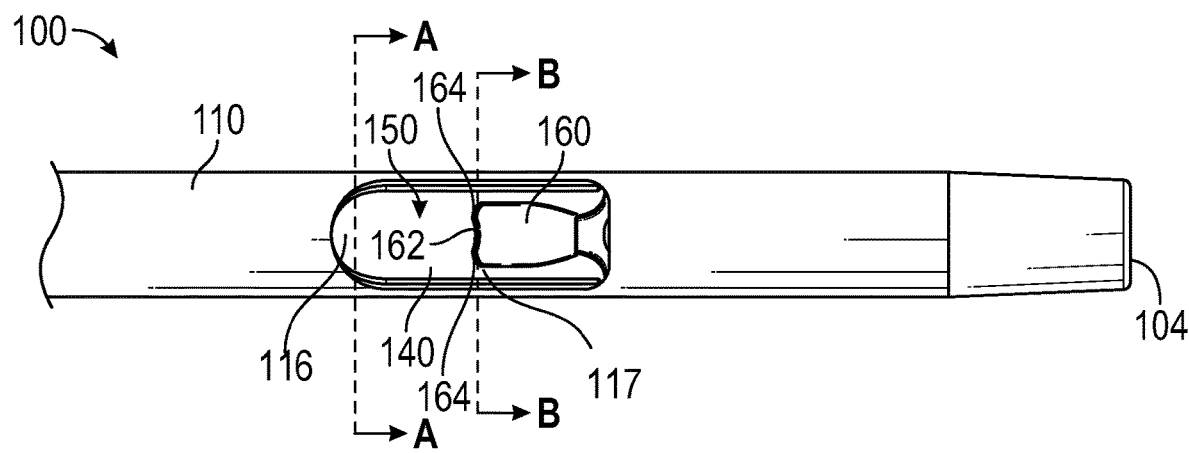
FIG. 3 illustrates a top view of a distal portion of a delivery device.
Figure 4:
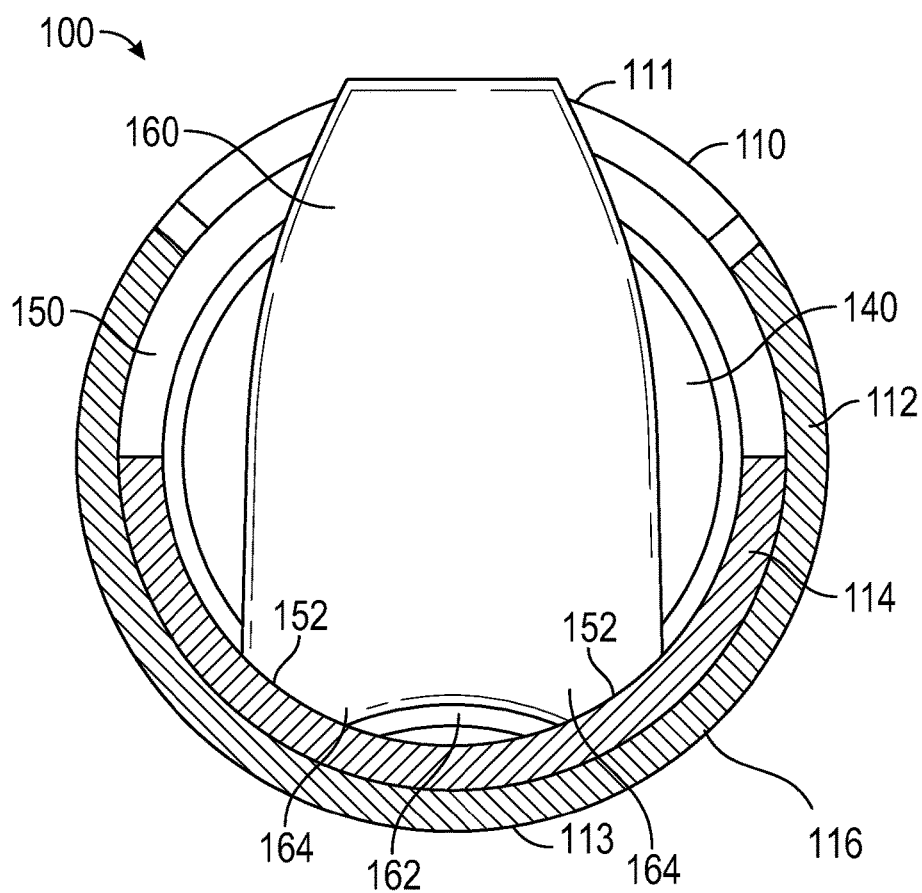
FIG. 4 illustrates a sectional view of a distal portion of a delivery device, taken along line A-A of FIG. 3.

Referring now to FIGS. 2-4, the shaft 110 can be or include a catheter shaft lined with an inner layer (e.g., PTFE, hydrophilic coating, etc.) and/or jacketed with on outer layer (e.g., polymers, stainless steel braiding, polyimide, etc.). The side port 150 can be formed in the shaft 110 at a location between the proximal end and the distal end portion 104 of the delivery device 100. The side port 150 connects the lumen 140 to a space laterally adjacent to the shaft 110. The side port 150 can be molded, laser cut or otherwise formed into the shaft 110.

As shown in FIGS. 2 and 3, a flap member 160 can be positioned at or near the side port 150. For example, the flap member 160 can extend from a portion of the shaft 110 that is adjacent to the side port 150. The flap member 160 can at least partially extend into the lumen 140 in at least one configuration thereof. The flap member 160 can be integrally formed (e.g., monolithic) with at least a portion of the shaft 110 and/or securely coupled thereto. As used herein, a monolithic structure is one that is integrally formed of a single piece of material, rather than of separate pieces that are joined together by an interface. For example, the flap member 160 and the shaft 110 can be a unibody and/or unitary structure. By providing a monolithic, unitary, and/or unibody flap member 160 and shaft 110, these components need not contain interfaces or discontinuities, such as those that occur in assembled parts. Accordingly, the monolithic, unitary, and/or unibody flap member 160 and shaft 110 can be fabricated to more precise and consistent dimensions as well as provide greater structural support.

The flap member 160 can include a metal, such as a shape memory alloy (e.g., Nitinol). The flap member 160 can be heat set (e.g., annealed) into a position and/or configuration such that it is biased to such a configuration (e.g., first position) in the absence of an external force that deflects the flap member 160.

As shown in FIG. 4, in at least one configuration, the flap member 160 can extend from the shaft 110 into the lumen 140. The flap member 160 can block at least a portion of the lumen 140 for objects traveling along the longitudinal axis 108 of the delivery device 100 (e.g., within the lumen 140). The flap member 160 can be positioned and shaped to allow objects to stay within the lumen 140 when crossing the flap member 160 when such objects approach the flap member 160 from one side thereof. The flap member 160 can be positioned and shaped to deflect objects out of the lumen 140 and through the side port 150 when crossing the flap member 160 when such objects approach the flap member 160 from another side thereof.

As further shown in FIG. 4, the flap member 160 can include a terminal end that facilitates interaction with and passage of a guidewire 200 or other interventional device. For example, the terminal end can include a concave shape that receives a portion of the guidewire 200. Such a shape can help direct the guidewire 200 to a preferred position with respect to the flap member 160 and maintain the guidewire 200 in a particular position within the lumen 140 (e.g., radially and/or circumferentially) while the guidewire 200 travels longitudinally within the lumen 140.

Figure 5:
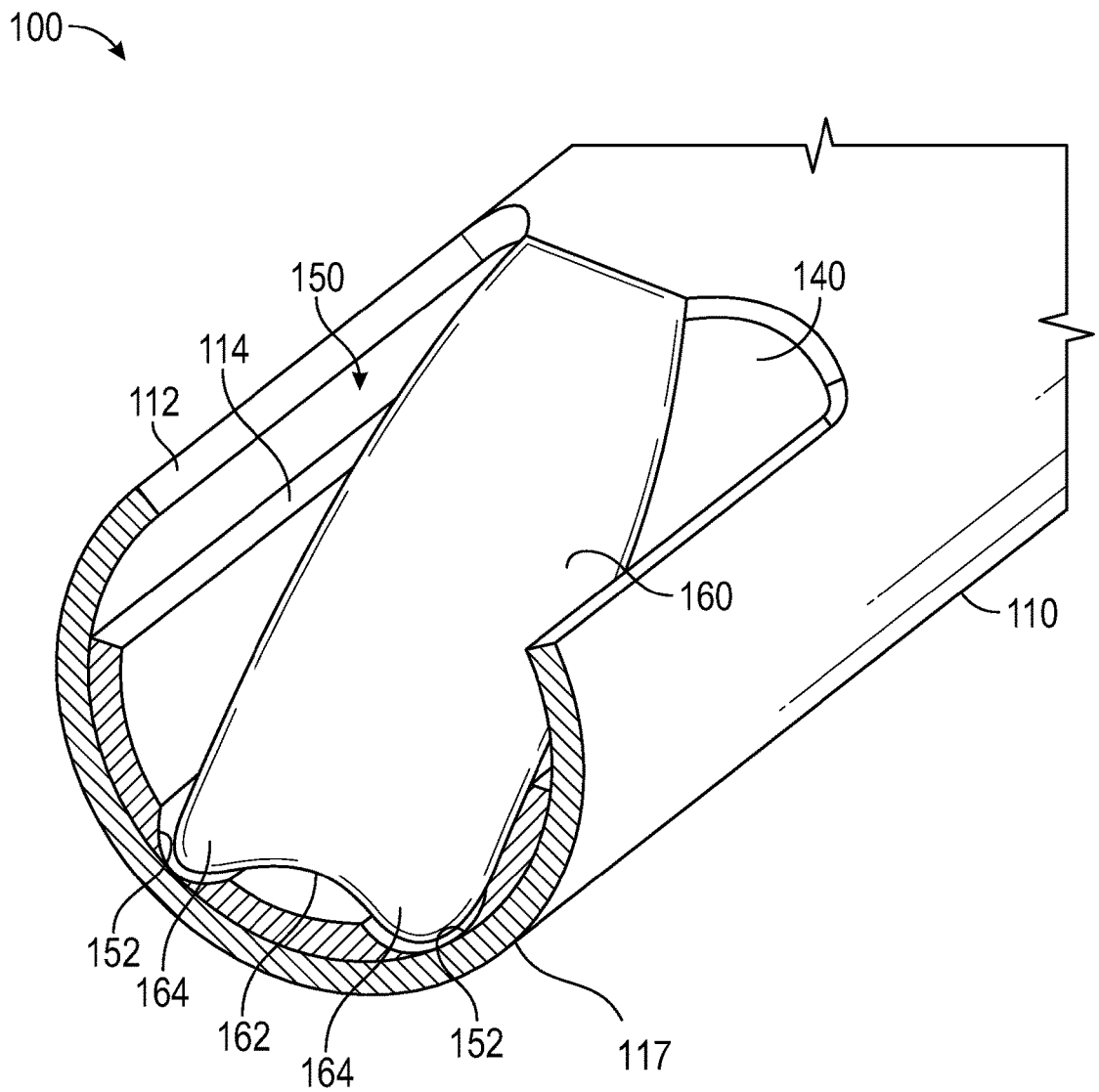
FIG. 5 illustrates a perspective sectional view of a distal portion of a delivery device, taken along line B-B of FIG. 3.

As shown in FIGS. 3-5, the concavity of the flap member 160 can be defined, at least in part, by a curvature having an apex 162 and protruding ends 164. For example, the apex 162 can be defined at a central or middle region of the terminal end of the flap member 160. On either side (e.g., lateral side) of the apex, the flap member can define protruding ends 164 that extend further from the side port 150 (e.g., at an attachment region at the shaft 110) than does the apex 162. As such, the protruding ends 164 can extend a further distance within and across the lumen 140 than does the apex 162.

As shown in FIGS. 3-5, the flap member 160 can extend from a location at or near the side port 150 and into the lumen 140 of the shaft 110. The flap member 160 can extend from a first radial side 111 of the shaft 110 to a second radial side 113 of the shaft and at least to an interior surface of the shaft 110 that is opposite the side port 150. While a first longitudinal portion 116 of the shaft 110 can define an inner diameter, the flap member 160 can extend radially beyond an inner diameter of the first longitudinal portion 116 of the shaft 110 to protrude into a recess of the shaft 110. For example, the shaft 110 can include an outer tube 112 and an inner tube 114 that is radially within the outer tube 112. The inner tube 114 can define an inner diameter at a first longitudinal portion 116 thereof (see FIG. 4). As shown in FIG. 4, the inner diameter can have a curvature that is defined, in cross section, by portions thereof being substantially equal distances from the longitudinal axis 108 of the shaft 110. It will be understood that such a curvature can be formed without extending entirely radially about the central axis, such as where interrupted by the side port 150. Such a curvature can be congruent with an outer diameter of the shaft 110 (i.e., an outer diameter of the outer tube 112), an inner diameter of the outer tube 112, and/or an outer diameter of the inner tube 114. As shown in FIG. 5, in a second longitudinal portion 117 of the shaft 110, the inner tube 114 can form one or more recesses 152 that extend radially outwardly beyond the inner diameter of the first longitudinal portion 116 shown in FIG. 4. In some embodiments, the recesses 152 can each have a shape that is complementary to a corresponding shape of the flap member 160, such as the protruding ends 164 of the flap member 160. The terminal end of the flap member 160, for example with the protruding ends 164, can extend into the recesses 152 formed by the inner tube 114. As such, the flap member 160 (e.g., with the protruding ends 164) can extend radially beyond an inner diameter defined by the shaft 110 (e.g., at the first longitudinal portion 116). Such an arrangement can allow the concave shape of the flap member 160 to be provided while also allowing the flap member 160 to provide substantial coverage across the lumen 140. In particular, the shaft 110 can form a concave shape with the inner diameter thereof, for example at the inner tube 114. The concave shape of the terminal end of the flap member 160 can extend to such a concave surface of the shaft 110. By providing the ability for portions of the flap member 160 to extend beyond the inner diameter of the shaft 110, the flap member 160 can leave a small or minimal space between the terminal end thereof and the inner diameter of the shaft 110. This helps provide coverage for effectively deflecting objects and materials that are incident on the upward facing side of the flap member 160 (e.g., side shown in FIGS. 3-5) toward the side port 150, as described further herein. The small or minimal space between the flap member 160 and the inner diameter of the shaft 110 helps ensure that even small or pointed ends of such objects and materials are acted upon by the flap member 160 rather than bypassing the flap member 160. With the same arrangement, objects and materials that are incident on the opposing or downward facing side of the flap member 160 can interact with the flap member 160. Such interactions can include deflecting the flap member 160 toward the side port 150 and nesting within the concave shape (e.g., at the apex 162 and/or between the protruding ends 164) of the terminal end of the flap member 160, as described further herein.

Figure 6:
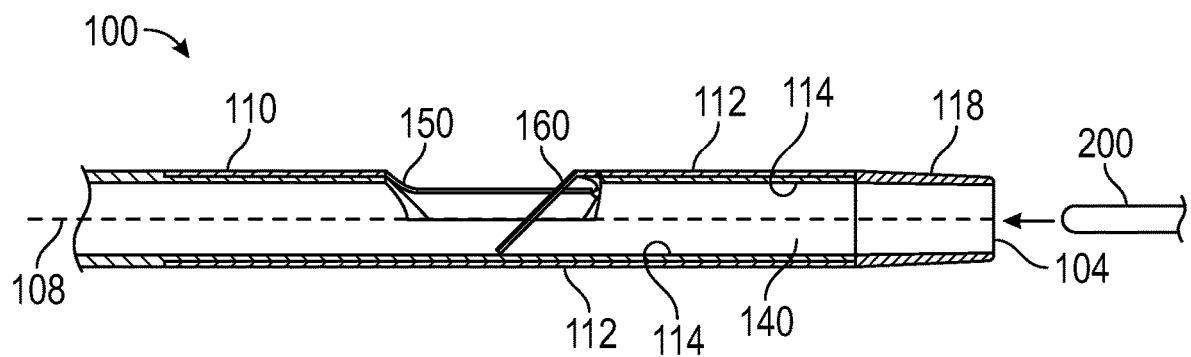
FIG. 6 illustrates a side sectional view of a delivery device and a guidewire.

Referring now to FIGS. 6-9, the delivery device 100 can be operated to facilitate positioning of other devices with respect to a body vessel and/or objects therein (e.g., CTO). As shown in FIG. 6, a guidewire 200 can be inserted through the distal end portion 104 of the delivery device 100. As the guidewire 200 passes the flap member 160, the flap member 160 can deflect as needed to allow passage of the guidewire 200 through the lumen 140 and beyond the flap member 160. Furthermore, the flap member 160 can maintain the guidewire 200 within the lumen 140 and prevent the guidewire 200 from exiting the shaft 110 through the side port 150. As such the guidewire 200 can be directed to the proximal end of the delivery device 100 for operation by a user at the proximal end.

Figure 7:
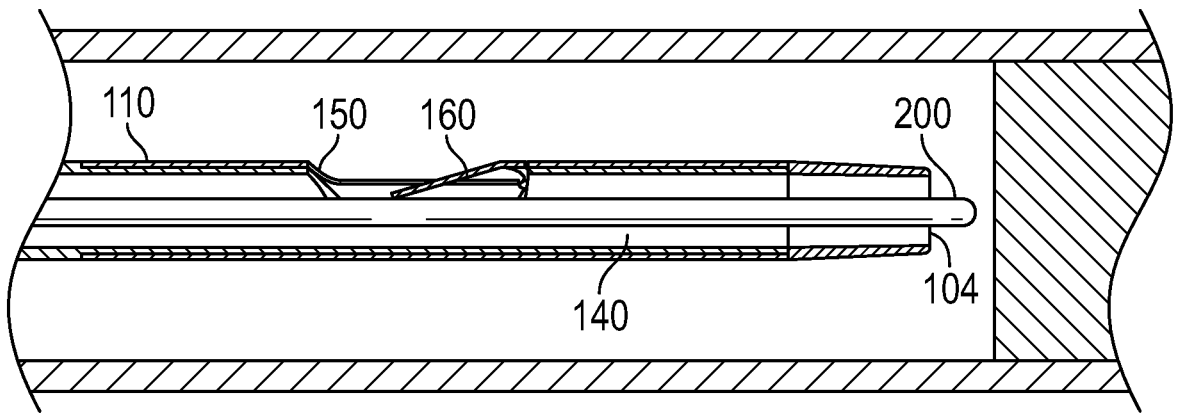
FIG. 7 illustrates a side sectional view of the delivery device in a body vessel with the guidewire extending out a distal end of the delivery device.

As shown in FIG. 7, the delivery device 100 and the guidewire 200 can be positioned within an anatomy of the patient (e.g., within a blood vessel and adjacent to an occlusion 180). At least a portion of the guidewire 200 can remain within the lumen 140 and distal to the flap member 160. As such, the flap member 160 can remain in a deflected (e.g., second) position. The guidewire 200 can be operated to penetrate the occlusion. Additionally or alternatively, another device (e.g., coupled to the guidewire 200 and/or inserted through the proximal end of the delivery device) can be operated to penetrate the occlusion. The guidewire 200 and/or another device can be moved within the lumen 140 and maintain a position partially distal to the flap member 160 by limiting its proximally directed retraction.

Figure 8:
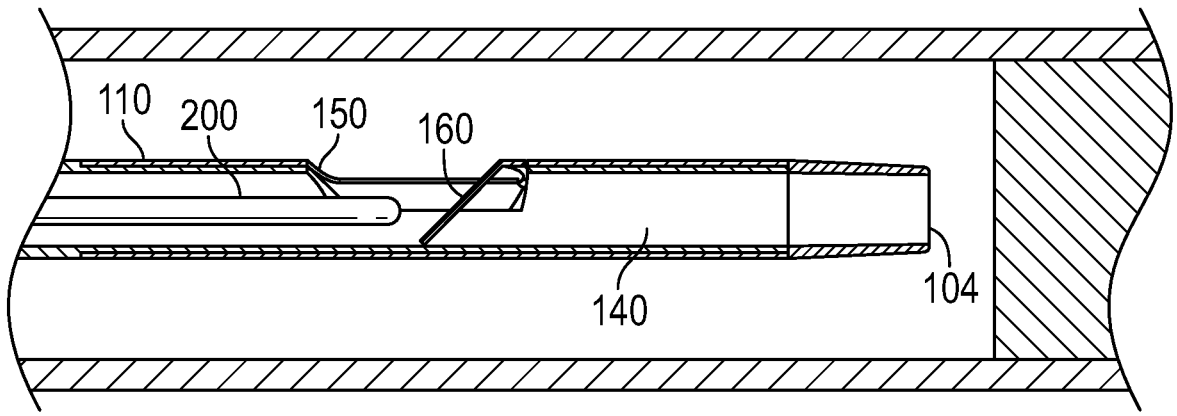
FIG. 8 illustrates a side sectional view of the delivery device with the guidewire retracted proximally within the delivery device.

As shown in FIG. 8, the guidewire 200 can be operated to facilitate sub-intimal penetration and/or crossing of the occlusion. The guidewire 200 can be retracted proximally to be entirely proximal to the flap member 160. When the guidewire 200 is no longer spanning the flap member 160, the flap member 160 can return to a biased (e.g., first) position, in which it blocks at least a portion of the lumen 140.

Figure 9:
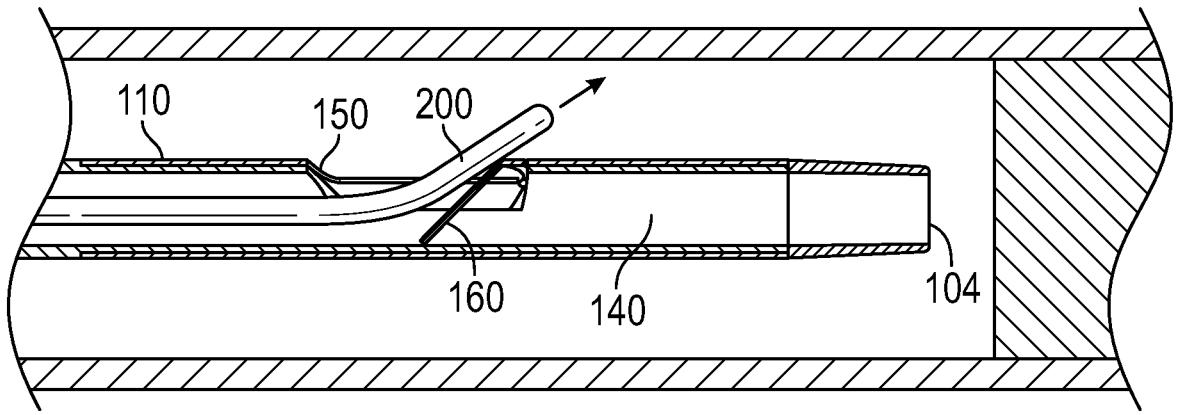
FIG. 9 illustrates a side sectional view of the delivery device with the guidewire extending out of a side port of the delivery device.

As shown in FIG. 9, the flap member 160 can direct the guidewire 200 through the side port 150. The guidewire 200 can be advanced distally until it contacts the flap member 160. The flap member 160, in its biased position, can provide a surface that directs the guidewire 200 away from the lumen 140, through the side port 150, and toward the vessel wall. For example, the flap member 160 can form an oblique (i.e., neither parallel nor perpendicular) angle with respect to the longitudinal axis 108 of the shaft 110. Accordingly, by advancing the guidewire 200 longitudinally against the flap member 160, the flap member 160 redirects the guidewire 200 out of the side port 150 and in a direction that forms an oblique angle with respect to the longitudinal axis 108 of the shaft 110.

The guidewire 200 can be operated to penetrate the vessel wall. Additionally or alternatively, another device (e.g., coupled to the guidewire 200 and/or inserted through the proximal end of the delivery device) can be operated to penetrate the vessel wall. Such penetration can allow the guidewire 200 to travel around the occlusion 180, thereby providing access to an opposite side thereof. Such access can be used to restore and enhance flow across the occlusion 180.

Additionally or alternatively, the guidewire 200 can be used with or replaced by an interventional device in one or more of the steps described herein and/or in an additional step. An example of such an interventional device is the crossing device disclosed in International Patent Application No. PCT/US2010/047170, filed Aug. 30, 2010, entitled "SYSTEMS, METHODS AND DEVICES FOR ABLATION, CROSSING, AND CUTTING OF OCCLUSIONS," which is incorporated herein by reference in its entirety. For example, an interventional device can be actuated (e.g., advanced, retracted, rotated, etc.) and provide features (e.g., blades, edges, cutting implements, etc.) that facilitate penetration or other actions with respect to the target anatomy (e.g., CTO, vessel wall, etc.).

A delivery device can include any number of side ports 150 and flap members 160. The different side ports 150 and flap members 160 can be proximal to, distal to, and/or axially overlapping each other. The different side ports 150 and flap members 160 can be on a same or different radial side with respect to each other. Devices (e.g., guidewires, interventional devices, etc.) extending through different side ports can extend through the same proximal end and/or lumen of a shaft or through different locations.

Figure 10:
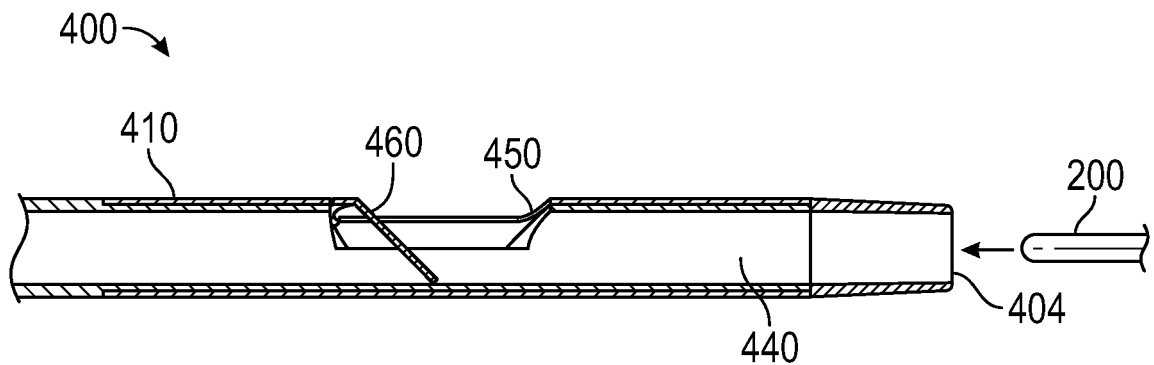
FIG. 10 illustrates a side sectional view of a delivery device and a guidewire in a rapid exchange configuration.
Figure 11:
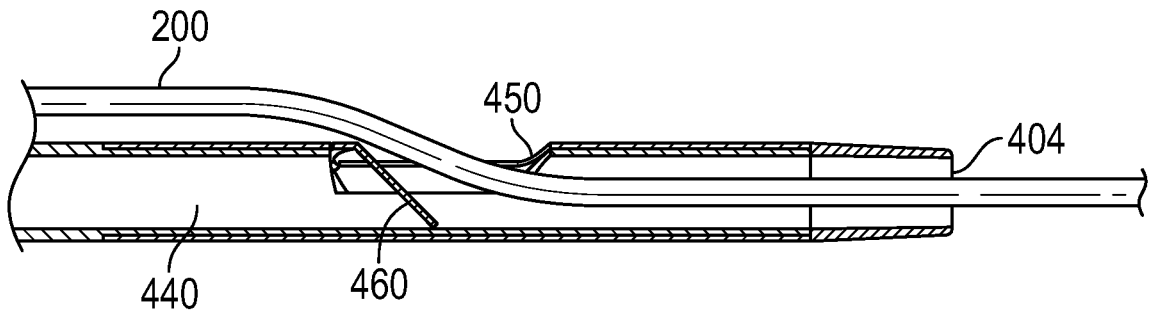
FIG. 11 illustrates a side sectional view of the delivery device with the guidewire extending through a distal end and a side port of the delivery device.
Figure 12:
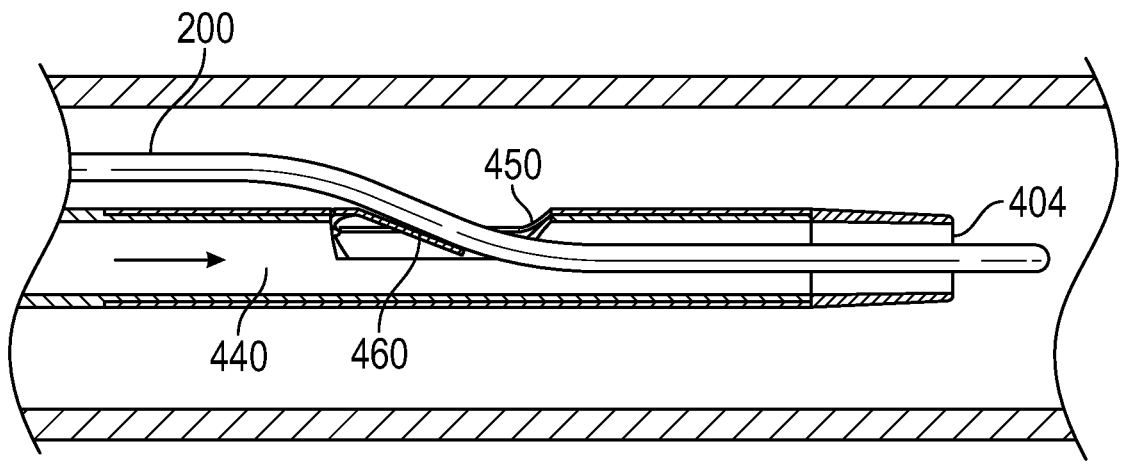
FIG. 12 illustrates a side sectional view of the delivery device in a body vessel with the guidewire extending through the distal end and the side port of the delivery device.

Referring now to FIGS. 10-12, a delivery device 400 can be operated to facilitate operation of devices and/or fluid flow with respect to a body vessel and/or objects therein (e.g., CTO). As shown in FIG. 10, a guidewire 200 can be inserted through the distal end 404 of the delivery device 400. Such an operation can be performed while the delivery device 400 is outside the patient.

As shown in FIG. 11, the flap member 460 can direct the guidewire 200 through the side port 450. The guidewire 200 can be advanced proximally until it contacts the flap member 460. The flap member 460, in its biased position, can provide a surface that directs the guidewire 200 away from the lumen 440 and through the side port 450.

As shown in FIG. 12, the delivery device 400, along with the guidewire 200, can be positioned within an anatomy (e.g., blood vessel) of the patient.

At least a portion of the guidewire 200 can remain within the lumen 140 and distal to the flap member 160. The guidewire 200 and/or another device can be moved within the lumen 140 and/or alongside the shaft 410.

Fluid can be provided through the lumen 440 for injection into the target anatomy. For example, the fluid can be provided at the proximal end of the delivery device 400 and through the lumen 440. As the flow of fluid is incident upon the flap member 460, the flap member 460 can deflect as needed to allow passage of the fluid through the lumen 440 and beyond the flap member 460. Furthermore, the flap member 460 can maintain at least some of the fluid within the lumen 440 and prevent at least some of the fluid from exiting the shaft 410 through the side port 450. As such the fluid can be directed to the distal end 404 of the delivery device 400 for injection. Such operations can be performed while the guidewire 200 and/or another device remains at least partially within the lumen 440 (e.g., distal to the flap member 460 and/or the side port 450).

A delivery device can include any number of side ports 450 and flap members 460. The different side ports 450 and flap members 460 can be proximal to, distal to, and/or axially overlapping each other. The different side ports 450 and flap members 460 can be on a same or different radial side with respect to each other. Devices (e.g., guidewires, interventional devices, etc.) extending through different side ports can extend through the same distal end and/or lumen of a shaft or through different locations.

While the delivery device 100 and the delivery device 400 are shown as separate devices, it will be understood that a single delivery device can include one or more of each of a side port 150, a flap member 160, a side port 450, and/or a flap member 460. The side port 150 and the flap member 160 can be proximal to, distal to, and/or axially overlapping the side port 450 and the flap member 460. The side port 150 and the flap member 160 can be on a same or different radial side with respect to that of the side port 450 and the flap member 460.

Vessels in which the delivery devices described herein may be sized and shaped for placement include arteries, such as coronary arteries, peripheral arteries, carotid arteries, circle of willis, anterior cerebral artery, middle cerebral artery, posterior cerebral artery, any of the lenticulostriate arteries, renal arteries, femoral arteries, veins, such as cerebral veins, saphenous veins, arteriovenous fistulas, or any other vessel that may contain a treatment site. Other vessels are likewise contemplated, and the delivery devices can be formed and/or selected according to a known destination and/or travel pathway within the body of a patient.

Accordingly, the systems and methods described herein provide multiple functions at different stages. By providing different functionality at different stages, the need to exchange and replace tools at different stages can be reduced or eliminated. Accordingly, such operations can be completed more rapidly, efficiently, and safely.

According to embodiments, a crossing device is disclosed, comprising, in combination a body coupled to a microcatheter at a proximal end of the microcatheter; a handle coupled to a blade at a proximal end of the blade, the blade disposed within a lumen of the microcatheter; wherein a sharpened tip of the blade is configured to advance from a natural position within the lumen of the microcatheter to an extended position beyond a distal end of the microcatheter as the handle is advanced relative to the body.

The crossing device may further comprise a spring configured to compress as the handle is advanced relative to the body; wherein the spring is configured to expand and retract the blade relative to the microcatheter as the handle is released.

The crossing device may further comprise a luer configured to attach to a proximal end of the handle and provide adaptable use of a supplemental treatment device in combination with the crossing device. The luer may be configured to guide a supplemental treatment device to the lumen of the microcatheter or a lumen of the blade. The supplemental treatment device may be at least one of a guidewire, a PTA balloon, and a stent device.

The tip of the blade may be disposed at a distal end of the blade and is of a rigid material. The tip of the blade may be a hollow, sharpened, everted tip.

The handle and the body may be configured to limit the expansion of the spring and provide the natural position of the blade and further configured to selectively lock the blade in at least one of the natural position and the extended position. The body may further comprise a nose detachable from the body and secured to the microcatheter, such that the microcatheter is selectively removable from the body.

According to embodiments, an improved surgical method for addressing blockage within a vessel is disclosed, comprising, in combination delivering an apparatus including at least a microcatheter to a desired treatment situs; positioning the microcatheter having at least a blade proximate to a surface of an occlusion, wherein the microcatheter is attached to a body and comprises a lumen; providing the blade within the lumen of the microcatheter to the surface of the occlusion, wherein the blade is attached to a handle; advancing the blade to an extended position by manipulation of the handle relative to the body; and retracting the blade to a natural position by releasing the handle.

The blade may be retracted by a spring between the handle and the body. The method may result in reconfiguration of at least a portion of the occlusion, whereby a different flow condition may be achieved.

The method may further comprise advancing the microcatheter and the blade through a channel created by advancement of the blade to an extended position. The method may further comprise providing a supplemental treatment device to the occlusion through a lumen of the blade. The supplemental treatment device may be at least one of a guidewire, a PTA balloon, and a stent device.

According to embodiments, a kit is disclosed, comprising a crossing device further comprising a body coupled to a microcatheter at a proximal end of the microcatheter; a handle coupled to a blade at a proximal end of the blade, the blade disposed within a lumen of the microcatheter; wherein a sharpened tip of the blade may be configured to advance from a natural position within the lumen of the microcatheter to an extended position beyond a distal end of the microcatheter as the handle is advanced relative to the body; and directions for use.

The kit may further comprise a supplemental treatment device configured to be advanced within the lumen of the microcatheter. The kit may further comprise a luer disposed at a proximal end of the handle and configured to guide the supplemental treatment device into the lumen of the microcatheter. The supplemental treatment device may be at least one of a guidewire, a PTA balloon, and a stent device.

A system for addressing obstructions within lumens, comprising, in combination a body coupled to a microcatheter at a proximal end of the microcatheter; a handle coupled to a blade at a proximal end of the blade, the blade disposed within a lumen of the microcatheter; a luer configured to attach to a proximal end of the handle and provide adaptable use of a supplemental treatment device in combination with the crossing device; a spring configured to compress as the handle is advanced relative to the body; wherein a tip of the blade may be configured to advance from a natural position within the lumen of the microcatheter to an extended position beyond a distal end of the microcatheter as the handle is advanced relative to the body; wherein the spring may be configured to expand and retract the blade relative to the microcatheter as the handle is released.

The devices and methods discussed herein may be employed for medical treatment and in conjunction with other devices and methods for medical treatment, as known to those skilled in the art.

Where a patient is indicated for certain treatment, monitoring, or intervention or suffers from a disease, a lumen of a blood vessel or other fluid-bearing vessel may become occluded. For example, a chronic total occlusion ("CTO") or other partial or total obstruction of a blood vessel may occur or be the result of a thrombus, an embolism, atherosclerosis, or other disease that results in a blockage, restriction, or occlusion of fluid flow within a body. Often, during procedures, situations arise requiring immediate intervention, such as to address a CTO.

Where treatment of an occlusion by endovascular procedure is desired, medical professionals may attempt endovascular surgical procedures. Endovascular procedures include angioplasty procedures, stent placement, various scope procedures, and plethoric diagnostic, intermediary and interlocutory clot addressing schemes, which may include temporarily or permanently emplaced devices.

An occlusion may include a fibrous cap, composed of lipids, endothelial cells, macrophages, smooth muscle cells, foam cells, connective tissue, and other vascular materials. An occlusion may include calcification, such that the occlusion becomes hardened. Under these conditions, various endovascular procedures including thrombectomy, angioplasty, stent placement, retrieval of an obstruction, and others may be complicated or prevented by the difficulty or inability to penetrate the occlusion. For example, such procedures may require at least partial penetration of an occlusion before the procedure may be commenced or completed. Often, establishing some degree of reperfusion is critical.

According to embodiments, as shown in FIGS. 13, 14, 15, and 16, crossing device 1 may include body 13, microcatheter 21, handle 12, and blade 16. According to embodiments, crossing device 1 allows for a handheld mechanical penetration of an occlusion. Surgeons and interventionalists have expressed ongoing needs for devices leveraging their "hand" or feel for manipulating devices in situ.

Figure 13:
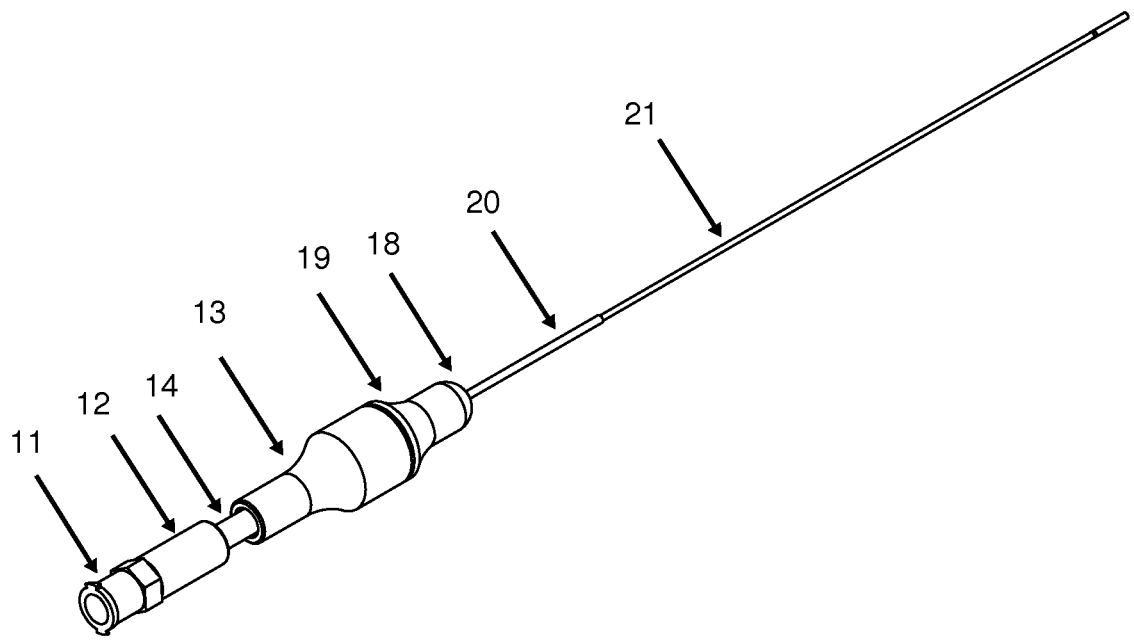
FIG. 13 is a schematic view of an embodiment of a crossing device in a natural position, according to embodiments of the present disclosure.
Figure 14:
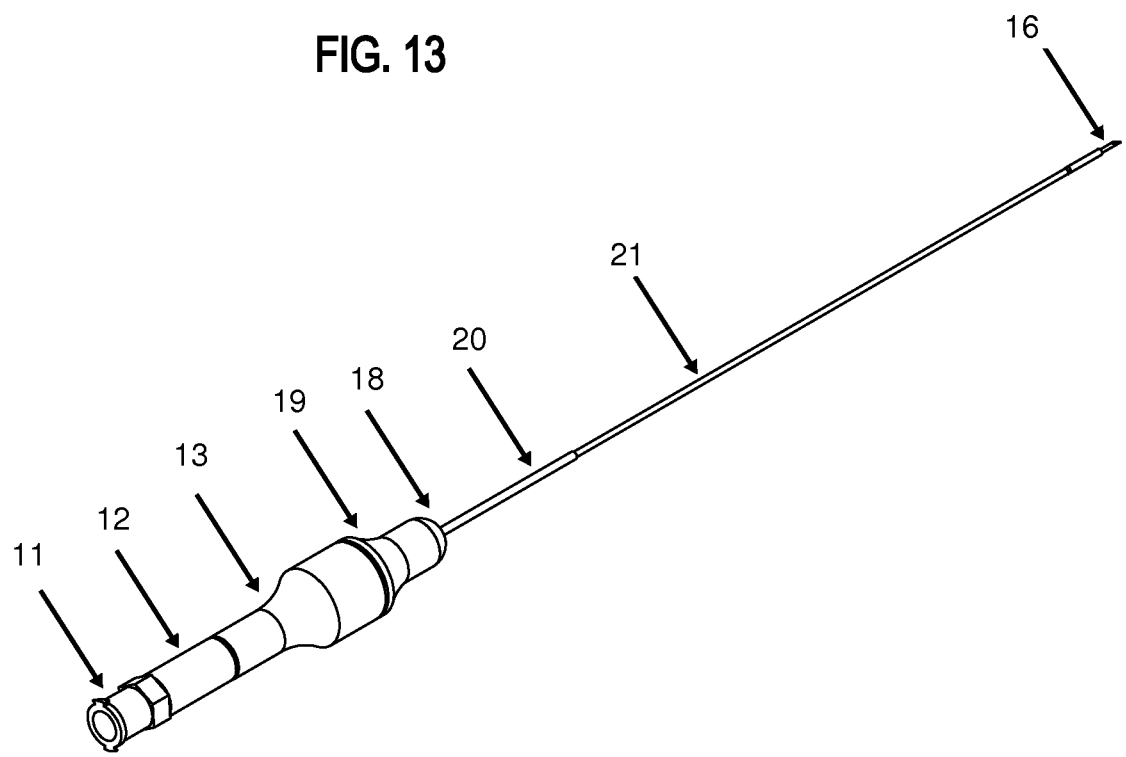
FIG. 14 is a schematic view of an embodiment of a crossing device in an extended position, according to embodiments of the present disclosure.
Figure 15:
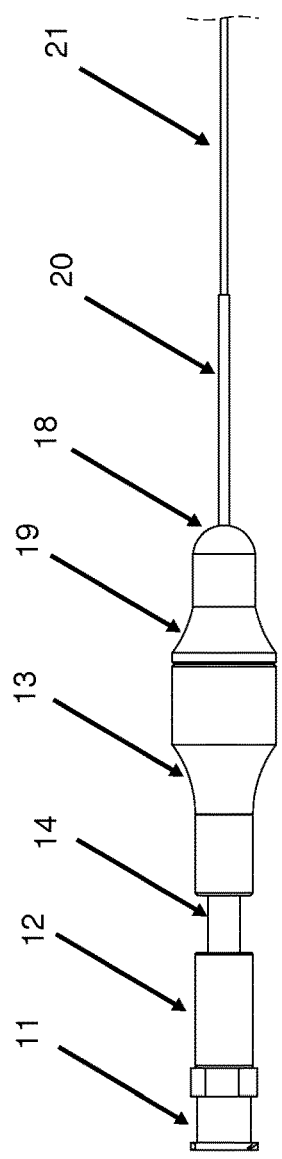
FIG. 15 is a schematic view of an embodiment of a crossing device in a natural position, according to embodiments of the present disclosure.
Figure 16:
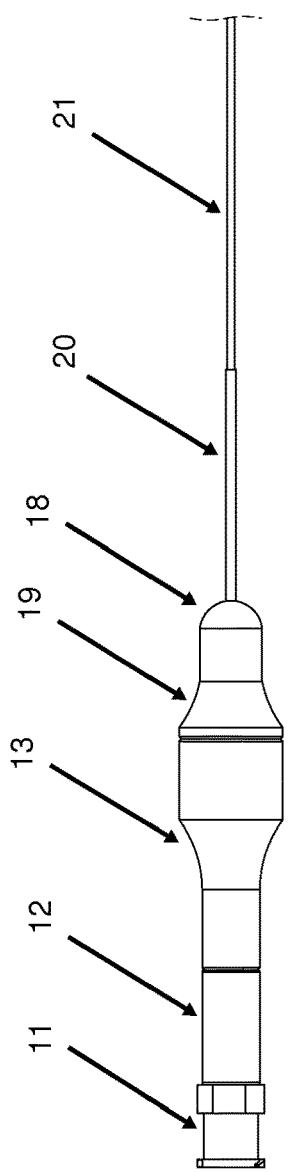
FIG. 16 is a schematic view of an embodiment of a crossing device in an extended position, according to embodiments of the present disclosure.

According to embodiments, body 13 may be attached to microcatheter 21, and handle 12 may be attached to blade 16, such that handle 12 is moveable relative to body 13, and movement of handle 12 relative to body 13 causes advancement and retraction of blade 16 along the inner portion of microcatheter 21. FIGS. 13 and 15 show crossing device 1 in a natural position, with handle 12 and blade 16 retracted; FIGS. 14 and 16 show crossing device 1 in an extended position, with handle 12 and blade 16 extended.

Figure 17:
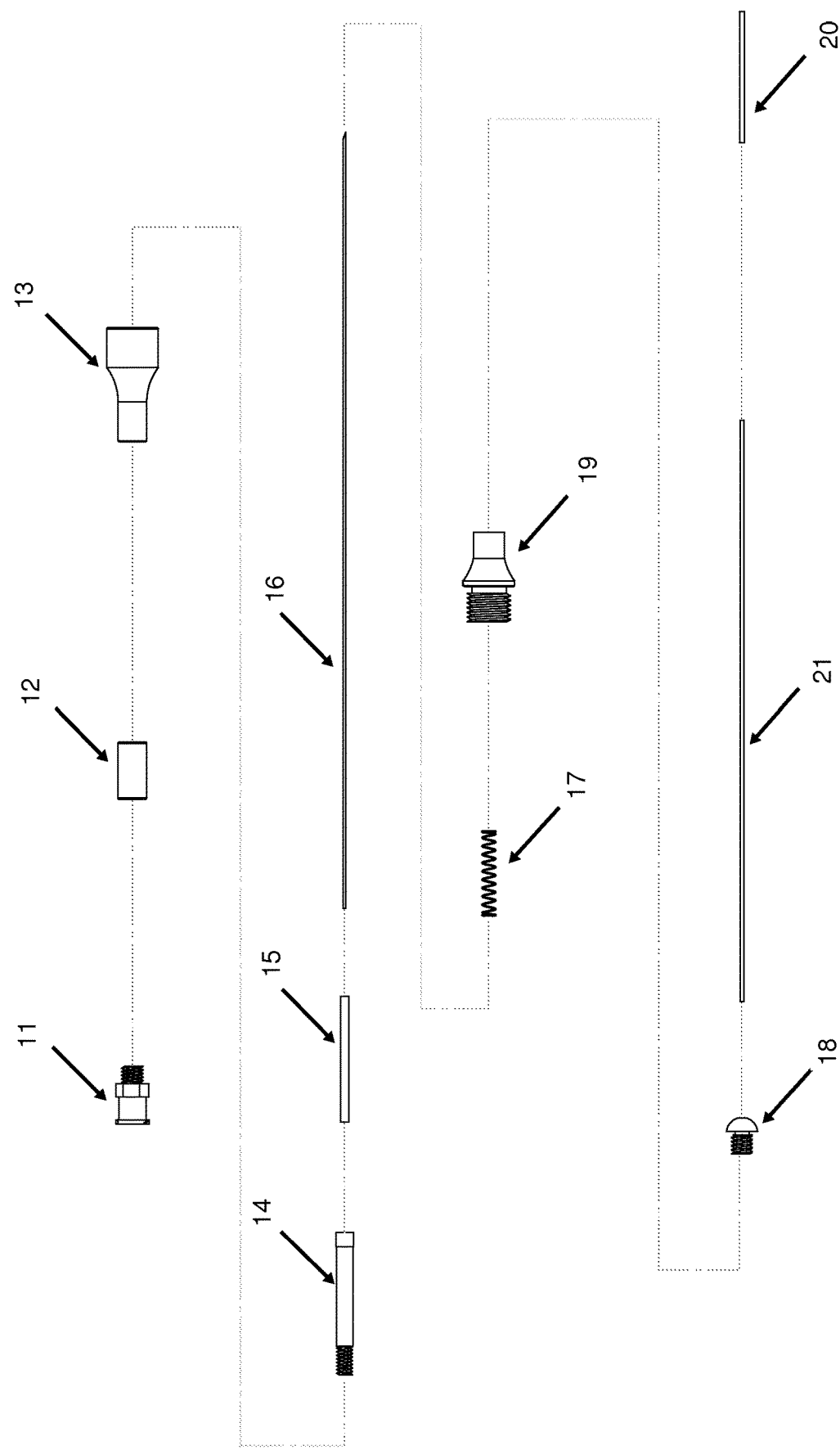
FIG. 17 is an exploded view of an embodiment of a crossing device, according to embodiments of the present disclosure.
Figure 18:
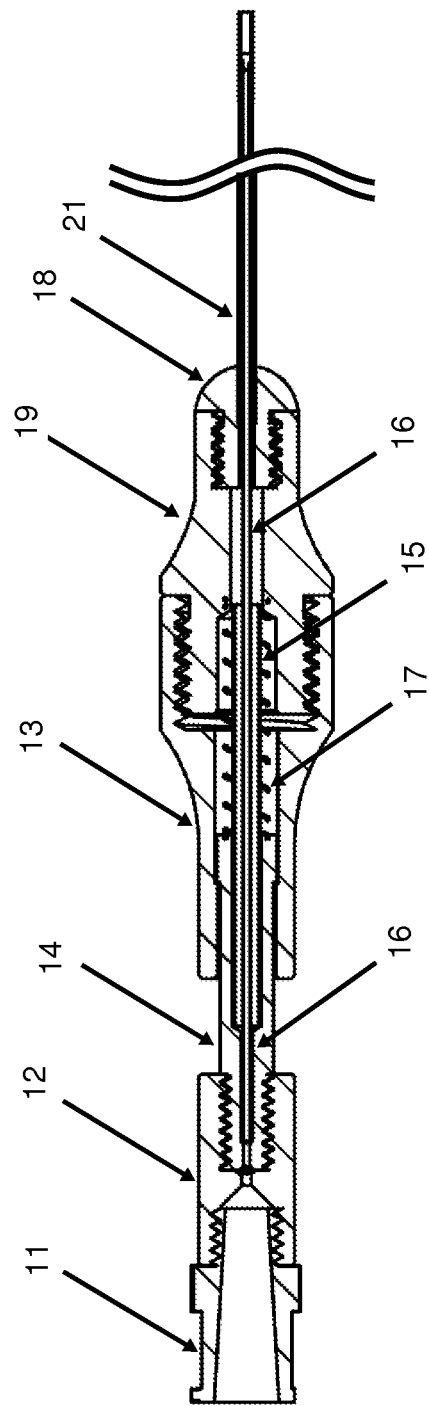
FIG. 18 is a cross-sectional view of an embodiment of a crossing device, according to embodiments of the present disclosure.

According to embodiments, handle 12 may include or be combined with one or more of luer 11, plunger rod 14, hypo support 15, and blade 16. For example, as shown in FIGS. 17 and 18, handle 12, luer 11, plunger rod 14, hypo support 15, and blade 16 may be combined to form an integrated unit. One or more interfaces (e.g., threading, etc.) or fixations (e.g., adhesive, epoxy, etc.) may be provided to combine said components.

According to embodiments, body 13 may include or be combined with one or more of nose guide 19, nose 18, heat shrink 20, and microcatheter 21. For example, as shown in FIGS. 17 and 18, body 13, nose guide 19, nose 18, heat shrink 20, and microcatheter 21 may be combined to form an integrated unit. One or more interfaces (e.g., threading, etc.) or fixations (e.g., adhesive, epoxy, etc.) may be provided to combine said components.

According to embodiments, spring 17 may be disposed between at least a portion of handle 12 and at least a portion of body 13. For example, as shown in FIG. 18, spring 17 extends between plunger rod 14—which is attached to handle 12—and nose guide 19—which is attached to body 13.

According to embodiments, spring 17 may tend to separate handle 12 from body 13 by way of elastic expansion. Handle 12 and body 13 may be configured to set a limit on the separation. For example, as shown in FIGS. 17 and 18, plunger rod 14 may include a flange that contacts a portion of body 13 to prevent travel along the axis beyond a certain point.

According to embodiments, nose 18 may be separate from and attachable to nose guide 19. Nose 18 may be fixably attached to microcatheter 21 and removably attached to nose guide 19, such that a microcatheter may be exchanged by removing nose 18. Such an option avoids the need to replace an entire system for need of a new microcatheter.

According to embodiments, crossing device 1 may facilitate use of a guidewire. Blade 16 may be configured with a hollow inner portion to allow a guidewire to be advanced from a proximal end of blade 16 to a distal end of blade 16. A guidewire lumen within blade 16 may be configured to accommodate any guidewire used for general vascular surgical procedures, such that a separate or distinct guidewire is not required for operation of crossing device 1.

According to embodiments, a luer 11 may be configured to interface with handle 12, as shown in FIGS. 17 and 5. Luer 11 may be a detachable hub/luer device configured to direct devices to microcatheter 21. Luer 11 may facilitate use of a support catheter, PTA balloon catheter, guidewire, or another lumen-configured or catheter-based supplemental treatment device to be exchanged with components of crossing device 1 during use, without removal of crossing device 1 from a patient. Such a configuration provides the ability to operate crossing device 1 in tandem or in sequence with other devices intended to deliver treatment to the same or nearby location.

According to embodiments, devices advanced within the lumen of blade 16 or otherwise provided through luer 11 may be operated, manipulated, and moved either along with or independent of handle 12, body 13, or their associated attached components.

According to embodiments, blade 16 may be configured to penetrate an occlusion upon contact with the occlusion. The distal end of blade 16 may include one of a variety of shapes to facilitate addressing the occlusion. Examples are shown in FIGS. 19 and 20. For example, blade 16 may include an everted end, an end with a sharpened tip, a concave end, a convex end, a coring tip, or other geometry to address an occlusion. Blade 16 may be hollow or solid.

According to embodiments, microcatheter 21 and blade 16 may provide sufficient flexibility to provide trackability within vessels of a patient. Microcatheter 21 and blade 16 may also provided sufficient rigidity to adequately transfer translational and rotational forces to be responsive at a distal end to a user located at a proximal end. According to embodiments, a tip at a distal end section of blade 16 may be relatively rigid, to provide a force of impact to an occlusion upon extension of the same.

According to embodiments, blade 16 may be configured to provide rotational motion at the point of deployment (e.g., at or near the distal end of crossing device 1). For example, as a user provides torque to handle 12, the torque may be translated along blade 16 to the distal end of blade 16. A torque provided at the distal end may improve treatment of the occlusion. The torque may be applied and translated before, during, or after extension of blade 16 beyond the distal end of microcatheter 21 and penetration of the occlusion.

According to embodiments, blade 16 may be configured to automatically rotate as it advances longitudinally relative to microcatheter 21. For example, threading may be provided about the axis along which blade 16 travels, such that travel of blade 16 along the axis also results in rotation of blade 16. For example, microcatheter 21 may be provided on at least a portion of its inner surface with threading, channels, or other guiding members to govern the manner in which blade 16 is advanced and retracted therein. Blade 16 may be provided with threading or other features to complement the guiding members of the axis along which blade 16 travels. For example, at least a portion of blade 16 may have a substantially spiral geometry adapted to interface with a complementary threading of microcatheter 21.

According to embodiments, blade 16 may be configured to penetrate or cross a section of an occlusion. According to embodiments, at least a portion of the occlusion may be captured or enclosed by features of blade 16. For example, ridges, protrusions, edges, and spiral geometries may be provided at the distal end of blade 16 to capture or enclose at least a portion of the occlusion that is penetrated by blade 16. Subsequently, blade 16 may be retracted, whereby at least a portion of the occlusion is removed by blade 16.

For example, where blade 16 includes a substantially spiral geometry, blade 16 may be advanced relative to microcatheter 21 with simultaneous longitudinal and rotational motion, whereby the spiral geometry captures at least a portion of the occlusion. Subsequently, blade 16 may be retracted longitudinally, whereby the portions of the occlusion are maintained within the spiral geometry. For example, blade 16 may be refracted with microcatheter 21. The foregoing may result in a path within the occlusion which may be the object of further operations, such as by the same device or others, or may be a path that at least partially restores a flow of blood and reperfusion through the occlusion.

According to embodiments, blade 16 may be configured to be entirely or almost entirely disposed within microcatheter 21 at its distal end when crossing device 1 is in a natural position, as shown in FIGS. 13 and 14, and to be somewhat extended beyond the distal end of microcatheter 21 when crossing device 1 is in an extended position, as shown in FIGS. 14 and 16.

According to embodiments, blade 16 may be configured to lock relative to microcatheter 21 when in a natural position or an extended position. Mechanisms to selectively or automatically lock and unlock blade 16 may be provided and may be operable by a user located at a proximal end of crossing device 1 to activate or deactivate said mechanisms.

According to embodiments, crossing device 1 may be configured as either an "over the wire" device (see FIG. 18) or a "rapid exchange" device (not shown). For example, supplemental devices may be configured to interface with crossing device 1 in a rapid exchange configuration. Crossing device 1 may include at least one lumen to accommodate a supplemental device to be used in conjunction with other components of crossing device 1. For example, a rapid exchange lumen may entry access at or near a proximal end of crossing device 1 and may extend to the distal end of crossing device 1 (e.g., the distal end of microcatheter 21).

According to embodiments, crossing device 1 may be used to address an occlusion. The distal end of crossing device 1, including a portion of microcatheter 21, blade 16, or a guidewire, may be brought to the location of an occlusion. For example, the guidewire may first be brought to the occlusion, followed by microcatheter 21 and blade 16. Blade 16 may be extended beyond the distal end of microcatheter 21 by operation of handle 12, as disclosed herein. As the occlusion is penetrated, increased advancement of microcatheter 21, blade 16, or a guidewire may be provided. Increased advancement of microcatheter 21, blade 16, or a guidewire may provide a improved position of the same to continue the crossing procedure in iterative steps. The process may be repeated in successive steps until the occlusion is crossed as desired.

According to embodiments, a method for causing blade 16 to penetrate an occlusion is disclosed. According to embodiments, microcatheter 21 may be brought to an occlusion, such as a heavily calcified lesion or other obstruction, as discussed herein. Blade 16 may be advanced by crossing device 1 such that it penetrates the occlusion. Blade 16 may retract when handle 12 is released, by the function of spring 17.

According to embodiments, the above described steps may be repeated as desired. For example, the above described steps may be repeated until the occlusion is entirely breached or until sufficient access is provided for other devices to act upon the occlusion. For example, a PTA balloon, stent device, or other catheter-based supplemental treatment device may operate within a channel created by operation of crossing device 1.

According to embodiments, the method and use of crossing device 1 may provide increased perfusion of fluid flow through the channel created by crossing device 1. The increased perfusion may provide improved conditions to facilitate breakdown of the occlusion, such that perfusion alone or in combination with other methods may remove threats presented by the occlusion.

According to embodiments, variations on embodiments may be made to provide customizable use and performance characteristics of crossing device 1. For example, spring 17 may be omitted such that handle 12 may travel relative to body 13 along the axis within certain limitations, such that the user may selectively and manually advance and retract blade 16 relative to microcatheter 21.

According to embodiments, crossing device 1 may be configured to allow blade 16 to be extended in a natural position and retracted based on action taken by a user (not shown). The configuration shown in FIG. 18 may be modified such that spring 17 is located such that its tendency toward elastic expansion causes handle 12 to be advanced toward body 13. In such a configuration, retraction of handle 12 may compress spring 17, such that release of handle 12 causes advancement of blade 16 toward or beyond the distal end of microcatheter 21.

According to embodiments, crossing device 1 may include two springs to provide novel use and performance characteristics (not shown). For example, one spring may tend toward extension of blade 16, and another spring may tend toward retraction of blade 16. Blade 16 may be configured such that the distal tip of blade 16 is in a desired location when equilibrium between the two springs is achieved in a natural position. A user may selectively advance or retract blade 16 by operation of handle 12, and release for blade 16 to allow release of any energy stored in the springs, with the blade 16 eventually reaching equilibrium in a natural position.

According to embodiments, a kit of parts is disclosed. One or more kits of parts can be envisioned by the person skilled in the art, the kits of parts including at least one component disclose herein and configured to perform at least one of the methods herein disclosed. Likewise, directions for use ("DFU") are included and the device may be part of a surgical tray or other packaged accessory set for surgeries. The kit may be a sub-component of a surgical tray.

Various examples of aspects of the disclosure are described below as clauses for convenience. These are provided as examples, and do not limit the subject technology.

Clause A: a delivery device comprising: a proximal end; a distal end; a shaft defining a lumen extending between the proximal end and the distal end; a side port extending through the shaft at a portion of the shaft that is between the proximal end and the distal end; and a flap member extending from the shaft on a distal side of the side port and toward the proximal end of the delivery device, the flap member being configured to transition from a first position blocking at least a portion of the lumen to a second position blocking at least a portion of the side port.

Clause B: a delivery device comprising: a proximal end; a distal end; a shaft defining a lumen extending between the proximal end and the distal end; a side port extending through the shaft at a portion of the shaft that is between the proximal end and the distal end; and a flap member extending from the shaft on a proximal side of the side port and toward the distal end of the delivery device, the flap member being configured to transition from a first position blocking at least a portion of the lumen to a second position blocking at least a portion of the side port.

Clause C: a method comprising: inserting a proximal portion of a guidewire through a distal end of a delivery device, into a lumen of the delivery device, and past a flap member of the delivery device; retracting the guidewire until a distal portion of the guidewire is proximal to the flap member; and advancing the guidewire until the flap member directs the distal portion of the guidewire out of the lumen and through a side port of the delivery device.

One or more of the above clauses can include one or more of the features described below. It is noted that any of the following clauses may be combined in any combination with each other, and placed into a respective independent clause, e.g., clause A, B, or C.

Clause 1: the flap member is biased toward the first position.

Clause 2: an interventional device extending within the lumen and across the side port, wherein the interventional device is retractable proximally to be entirely proximal to the flap member.

Clause 3: the flap member is biased toward the interventional device.

Clause 4: the interventional device is a guidewire.

Clause 5: while in the first position, the flap member extends from the side port to a wall of the shaft that is opposite the side port.

Clause 6: a terminal end of the flap member defines a concave shape.

Clause 7: the flap member forms an oblique angle with respect to a longitudinal axis of the shaft while in the first position.

Clause 8: an interventional device extending through the distal end of the delivery device, a length of the lumen that is distal to the side port, and the side port.

Clause 9: after the inserting and before the retracting: advancing the guidewire to a target anatomy; and advancing the delivery device over the guidewire to the target anatomy.

Clause 10: the flap member is biased to a first position blocking at least a portion of the lumen and away from a second position blocking at least a portion of the side port.

Clause 11: the inserting transitions the flap member from the second position to the first position.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

Generally, unless the context indicates otherwise, the terms "distal" and "proximal" within this disclosure reference a position relative to an operator or an operator's control device. For example, "proximal" can refer to a position closer to an operator or an operator's control device, and "distal" can refer to a position that is more distant from an operator or an operator's control device.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirements of the applicable patent law, nor should they be interpreted in such a way.

The invention claimed is:

1. A delivery device comprising:
   a proximal end;
   a distal end;
   a shaft defining a lumen extending between the proximal end and the distal end, a longitudinal portion of the shaft defining an inner diameter;
   a side port extending through the shaft at a portion of the shaft that is between the proximal end and the distal end; and
   a flap member extending from a first radial side of the shaft, the flap member being configured to transition between:
      a first position blocking at least a portion of the lumen with a terminal end of the flap member extending to a second radial side of the shaft and beyond the inner diameter defined by the longitudinal portion of shaft; and
      a second position blocking at least a portion of the side port.

2. The delivery device of claim 1, wherein the flap member is biased toward the first position.

3. The delivery device of claim 1, further comprising an interventional device extending within the lumen and across the side port, wherein the interventional device is retractable proximally to be entirely proximal to the flap member.

4. The delivery device of claim 3, wherein the flap member is biased toward the interventional device.

5. The delivery device of claim 3, wherein the interventional device is a guidewire.

6. The delivery device of claim 3, wherein the interventional device is a crossing device having a blade with a sharpened tip.

7. The delivery device of claim 1, wherein the terminal end of the flap member defines a concave shape having an apex and a pair of protruding ends on opposing sides of the apex.

8. The delivery device of claim 7, wherein the shaft defines recesses for receiving the protruding ends of the flap member.

9. The delivery device of claim 1, wherein the flap member forms an oblique angle with respect to a longitudinal axis of the shaft while in the first position.

10. The delivery device of claim 1, wherein the flap member extends distally from the shaft and towards the distal end of the delivery device.

11. The delivery device of claim 1, wherein the flap member extends proximally from the shaft and towards the proximal end of the delivery device.

12. A delivery device comprising:
a shaft defining a lumen, a longitudinal portion of the shaft having a first longitudinal portion defining an inner diameter and a second longitudinal portion defining recesses extending radially outwardly beyond the inner diameter of the first longitudinal portion;
a side port extending through the shaft; and
a flap member extending from the side port, wherein a terminal end of the flap member defines a concave shape having an apex and a pair of protruding ends on opposing sides of the apex, the flap member being biased to a configuration with the protruding ends within the recesses of the shaft.

13. The delivery device of claim 12, wherein the shaft comprises:
an outer tube; and
an inner tube within the outer tube and defining the recesses.

14. The delivery device of claim 13, wherein the flap member extends from the outer tube.

15. The delivery device of claim 12, wherein the flap member extends distally from the shaft and towards a distal end of the delivery device.

16. The delivery device of claim 12, wherein the flap member extends proximally from the shaft and towards a proximal end of the delivery device.

17. A method comprising:
inserting a proximal portion of a guidewire through a distal end of a delivery device, into a lumen of the delivery device, and past a flap member of the delivery device, the delivery device further including:
a proximal end;
a shaft defining the lumen extending between the proximal end and the distal end, a longitudinal portion of the shaft defining an inner diameter;
a side port extending through the shaft at a portion of the shaft that is between the proximal end and the distal end; and
the flap member extending from a first radial side of the shaft, the flap member blocking at least a portion of the side port;
retracting the guidewire until a distal portion of the guidewire is proximal to the flap member and the flap member extends from the first radial side of the delivery device, blocking at least a portion of the lumen, and with a terminal end of the flap member extending beyond the inner diameter defined by the longitudinal portion of shaft; and
advancing the guidewire until the flap member deflects the distal portion of the guidewire out of the lumen and through the side port of the delivery device.

18. The method of claim 17, further comprising, after the inserting and before the retracting:
advancing the guidewire to a target anatomy; and
advancing the delivery device over the guidewire to the target anatomy.

19. The method of claim 17, further comprising:
replacing the guidewire with an interventional device that comprises a blade;
advancing and rotating the interventional device to penetrate a target anatomy.

20. The method of claim 17, wherein the flap member is biased to a first position blocking at least a portion of the lumen and away from a second position blocking at least a portion of the side port, wherein the inserting transitions the flap member from the second position to the first position.

* * * * *